United States Patent [19]

Lustig et al.

[11] 4,173,828
[45] Nov. 13, 1979

[54] INTERCHANGEABLE TOOL OPERATING APPARATUS WITH PLURAL MOTION

[75] Inventors: Leopold P. Lustig, 304 Greenwood St., Newton Centre, Mass. 02159; Leonard L. Krasnow, Westboro, Mass.

[73] Assignee: Leopold Paul Lustig, Newton Centre, Mass.

[21] Appl. No.: 861,643

[22] Filed: Dec. 19, 1977

[51] Int. Cl.$^2$ .......................... A61C 3/06; A61C 1/10; E02D 7/02; B26B 1/00
[52] U.S. Cl. .................................. 433/87; 128/62 A; 173/29; 173/48; 30/123.3; 433/122; 433/126
[58] Field of Search ................... 32/46, 48, 53, 54, 28, 32/57-59, 27; 15/167 R; 401/280, 290; 128/62 A, 45, 54; 173/29, 47, 48, 75, 79; 30/123.3, 169

[56] References Cited

U.S. PATENT DOCUMENTS

| | | | |
|---|---|---|---|
| 2,738,528 | 3/1956 | Fridge, Sr. | 128/62 A |
| 2,990,739 | 7/1961 | Zifferer | 173/29 |
| 3,000,225 | 9/1961 | Taylor | 173/48 |
| 3,552,022 | 1/1971 | Axelsson | 128/62 A |
| 3,675,645 | 7/1972 | Samiran et al. | 128/62 A |
| 3,747,216 | 7/1973 | Bassi et al. | 32/57 |

Primary Examiner—Louis G. Mancene
Assistant Examiner—Michael Foycik
Attorney, Agent, or Firm—Alfred H. Rosen

[57] ABSTRACT

Novel tool operating apparatus is exemplified in a dental treatment device capable of driving alternatively at least a first tool and a second tool, each tool being intended to execute a different form of motion, with a single tool driving means to which each of several different tools can be removably coupled. The driving means includes a rotatable drive shaft fitted with tool engagement means in the form of a disc affixed to the shaft and lying in a plane that makes an acute angle with the rotational axis of the shaft. One tool can be fitted over the shaft to engage the disc so as to rotate the tool with the shaft. A second tool can be fitted over the shaft so that the shaft can rotate within the tool, but the tool will not rotate with the shaft. The second tool has means for cooperating with the shaft so as to execute an oscillatory motion relative to the shaft axis. Tools capable of two optional forms of oscillatory motion are disclosed—in one the motion is parallel to the axis of the shaft; in another the motion is nutational. The drive shaft can be provided with a fluid passage on its rotational axis through which to provide fluid such as a dental treatment agent to the tools, and each form of tool can be fitted with ducts for dispensing such an agent. Further tools suitable for endodontal use are disclosed.

34 Claims, 11 Drawing Figures

INTERCHANGEABLE TOOL OPERATING APPARATUS WITH PLURAL MOTION

BACKGROUND OF THE INVENTION

Motor-driven dental treatment devices have been used professionally, by dentists and dental hygienists, for a long time, and more recently they have been available for home use, and in portable forms using batteries that may be rechargeable. Examples are shown in U.S. Pat. Nos. 3,029,451; 3,145,404; 3,195,537; 3,220,039; 3,258,802; 3,275,919; 3,739,416; 3,757,419; 3,802,420; 3,921,298; 3,939,599; and 4,004,344. The prior devices provide a single form of motion; generally a rotatable brush or gum treatment tool is available; in some, tools for various purposes are available interchangeably. For example, U.S. Pat. No. 3,029,451 shows a dental tool 39 which can be formed for cleaning teeth or for gum massage, but in either case it rotates on a shaft 38; and U.S. Pat. No. 3,802,420 has as its object to provide a portable rotary hygiene device which is capable of removably mounting additional rotary work heads. In U.S. Pat. No. 3,848,336 a portable professional dental instrument shows provisions for interchanging prophylaxis tools and drills.

Dental stimulators are devices intended to be inserted between proximal surfaces of two adjacent teeth. The tapered rubber or plastic tip at the end of a toothbrush handle is a familiar example, which is shown in U.S. Pat. No. 2,141,969. Some have proposed to discharge cleaning fluids through an inter-proximal stimulator or massage implement; examples are shown in U.S. Pat. Nos. 2,187,560; 3,199,510; and 3,391,696. These are non-rotating devices for hand use only. Blasi U.S. Pat. No. 3,195,537 (mentioned above) shows a scheme for dispensing a dentifrice through a power driven rotary tooth cleaner and gum stimulator.

GENERAL NATURE OF THE INVENTION

The present invention provides a novel tool operating apparatus, exemplified in a dental treatment device capable of driving alternatively at least a first tool and a second tool, each tool being intended to execute a different form of motion. The device comprises essentially a single tool driving means to which each of several different tools can be removably coupled. The driving means includes a drive shaft journaled in a support for rotation around its longitudinal axis. A portion of the shaft extending from the support is fitted with tool engagement means. One tool can be fitted over the shaft to engage the tool engagement means so as to rotate the tool with the shaft. A second tool can be fitted over the shaft, with means on the tool to engage the support so that the shaft can rotate within the tool, but the tool will not rotate with the shaft. The second tool has means for cooperating with the shaft so as to execute an oscillatory motion relative to the shaft axis. Tools capable of two optional forms of oscillatory motion are disclosed—in one the motion is parallel to the axis of the shaft; in another the motion is nutational. A tool engagement means in the form of a disc affixed to the shaft and lying in a plane that makes an acute angle with the rotational axis of the shaft is useful for engaging and/or driving a variety of tools. The drive shaft can be provided with a fluid passage along its rotational axis through which to provide a fluid such as a dental treatment agent, an endodontic treatment material, or other fluid to the tools, and each form of tool can be fitted with ducts for dispensing such an agent or material.

The support mounting the drive shaft can be affixed in a separable fashion in known ways, to any available drive mechanism, such as an electric motor, and thereby is useable interchangeably with other motor-driven tool operating apparatus, dental instruments, and the like.

DETAILED DESCRIPTION OF THE DRAWINGS

Figure 1:
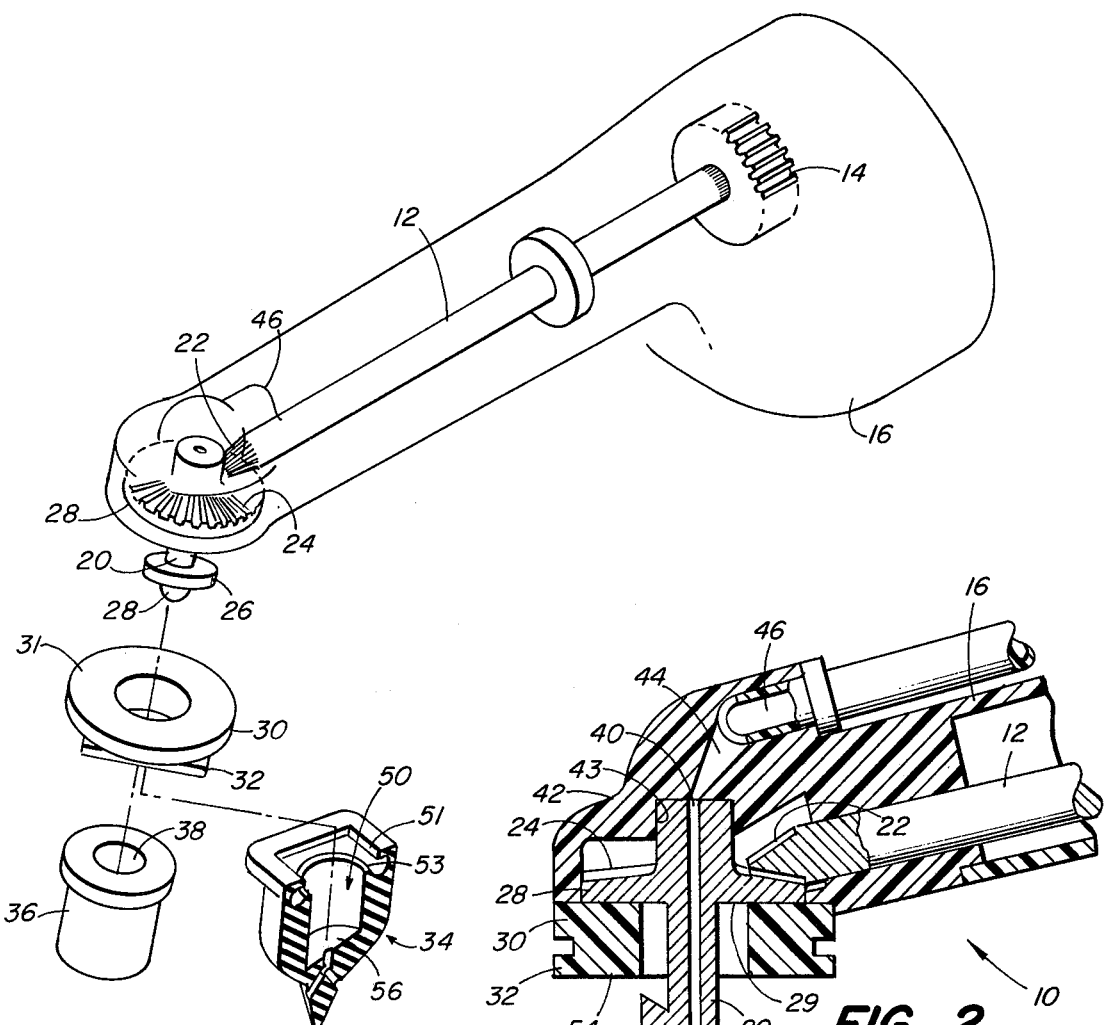
FIG. 1 is a partially-exploded view of a dental treatment device employing two different tools.

FIG. 1 is a partially exploded schematic view of a dental treatment device 10, having a transmission shaft 12 fitted with a driving gear 14 in a housing 16, all adapted to be fitted to a driving motor (not shown) as will be explained. The transmission shaft drives a tool drive shaft 20 via bevel gears 22,24 on the end of the transmission shaft and a geared disc 28 fitted to the tool drive shaft, respectively. The geared disc has gear teeth 24 on one side (upper side in the figure) and is smooth on the opposite side 29. A tool-engagement disc 26 is fixed to the tool drive shaft in a region between the lower extremity 28 and a housing part 30 which supports the geared disc 28 at its flat side. A rectangular flanged boss 32 is fitted to the outer side of the housing part 30, for holding one of the tools 34 non-rotatably attached to the device. The tool engagement disc 26 lies in a plane making an angle other than a right angle with the rotational axis of the tool drive shaft 20. Another of the tools 36 is adapted to engage the tool engagement disc via an aperture 38, so as to rotate with the tool drive shaft 20. The non-rotatable tool 34 has an aperture 50 into which the tool drive shaft 20 and tool engagement disc 26 can fit, for driving the non-rotatable tool in an oscillatory path, as will be explained with the aid of FIGS. 5 and 6.

Figure 2:
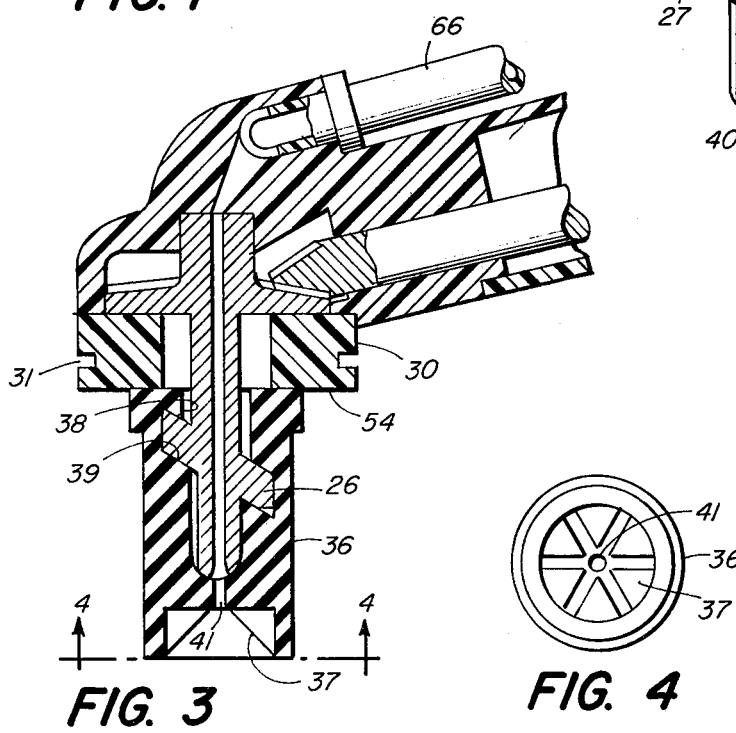
FIG. 2 is a partial section of FIG. 1 showing the common tool-driving means.
Figure 2A:
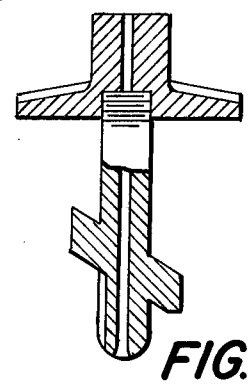
FIG. 2A shows an alternative structure for a component of FIG. 2.

FIG. 2 shows the tool holding part of the device 10, enlarged to show details of the tool drive shaft 20 and its supporting and driving mechanisms. The geared disc 28 and the tool drive shaft 20 are shown as one piece, with an axial bore 40 through it. The forward end 42 of the housing 16 has a passage 44 mating with the upper end (in the figure) of the bore 40, for passing a dentifrice or other oral treatment agent into and through the bore. Such an agent can be introduced at a receiving aperture 46, which may be fitted with a directional valve (not shown) as will be described. The housing parts 42 and 30 may be made of a rigid plastics material, and may be fixed together with a cement, as is known. They may alternatively be made of metal. The lower part 30 has an upper flat surface 31 on which the lower smooth surface 29 of the geared disc 28 can be supported for rotation; if desired a low friction washer (not shown) of a material such as Teflon can be located between the confronting surfaces 29 and 31. The tool drive shaft 20 and its geared disc 28, and the transmission shaft 12 are preferably made of metals suitable for small mechanical parts which should have high mechanical strength. While the tool drive shaft 20 and the geared disc 28 are shown as one part, the shaft 20 can be made separable from the disc 28, as by threading the shaft into the disc (FIG. 2A), if it is desired to provide interchangeably a plurality of different tool drive shafts. The tool engagement disc 26 is shown with a cylindrical peripheral surface 27 which enhances the utility of the device for some purposes, as will be explained with reference to FIGS. 5 and 6. The lower extremity 28 of the tool drive shaft may extend beyond the tool engagement disc a distance that is suitable for the variety of functions it is desired to achieve, as will also be explained. The upper extremity of the tool drive shaft 20 engages in a socket 43 in the upper housing part 42.

Figures 3, 4:
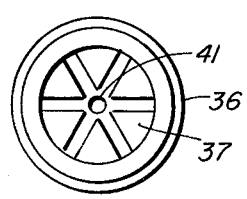
FIG. 3 is a similar section showing a rotational tool attached to the tool driving means.
FIG. 4 is an end view of the rotational tool on line 4—4 in FIG. 3.

Referring now to FIGS. 3 and 4, the rotatable tool 36 has a socket 39 within its aperture 38 for engaging the tool engagement disc 26; this socket embraces the periphery of the disc 26, so that the tool 36 rotates with the tool drive shaft 20. The rotatable tool has a bore 41 which registers with the bore 40 in the tool drive shaft, for conducting a treatment agent (when present) into a cup 37 at the lower extremity of the tool. At its upper end the rotatable tool abuts the lower surface 54 of the lower housing part 30.

The cup 37 has a design suitable for polishing teeth, or performing other oral or dental treatment, and may take any well-known form. As will be understood, the rotatable tool 36 can be made of soft rubber or a plastics material having similar resilient properties, so that it can be attached to the tool drive shaft 26, and removed from it, manually.

Figure 5:
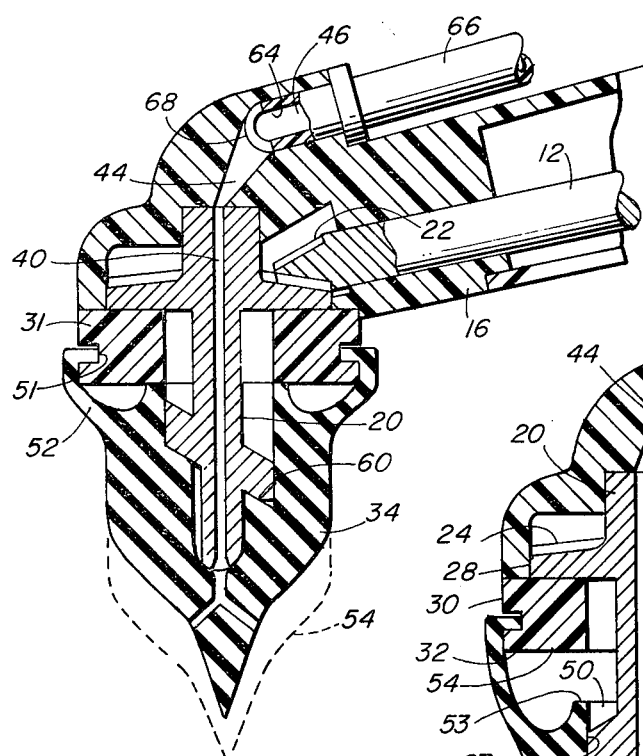
FIG. 5 is a similar section showing an oscillatory tool attached to the tool driving means, the tool being in a retracted position.
Figure 6:
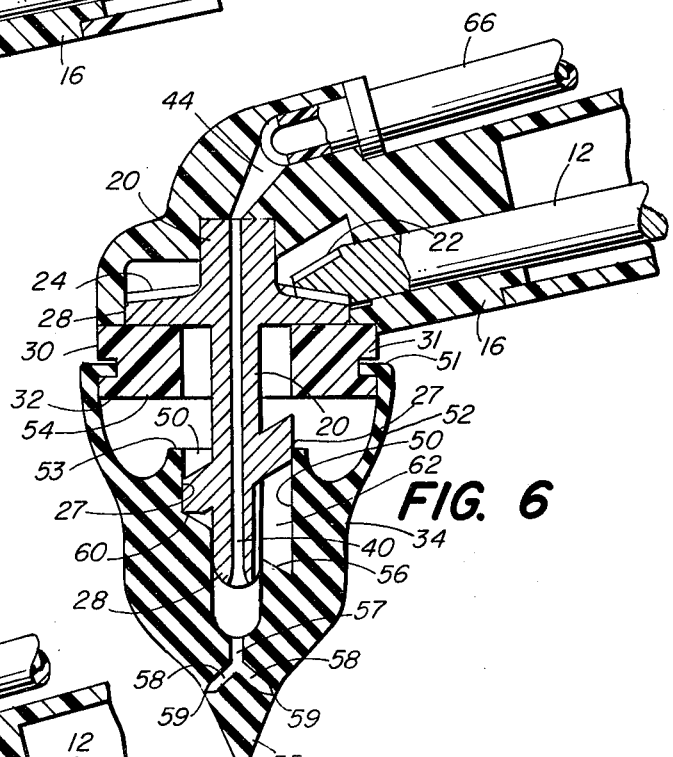
FIG. 6 is a view like FIG. 5 showing the oscillatory tool in an extended position.

FIGS. 5 and 6 show the non-rotatable tool 34 fitted to the tool drive shaft 20. This tool is intended to execute an oscillatory motion parallel to the rotational axis of the tool drive shaft when the latter is rotating. In executing this oscillatory motion the tool 34 is alternately retracted toward the lower housing part 30 to which it is attached, as is shown in FIG. 5, and extended from the housing part 30 as is shown in FIG. 6. The extended position is shown by a dashed line outline 54 in FIG. 5.

The non-rotatable tool 34 is fitted to the lower housing part 30 by engaging the flanged boss 32 with an inwardly facing rim 51 that fits in a groove 31 in the boss. Like the rotatable tool 36, the non-rotatable tool may be made of resilient rubber or a plastics material that is resilient, so that it can be manually fitted to the flanged boss 32, and removed from it. The boss is made rectangular in plan, so that the tool 34 cannot rotate around the rotational axis of the tool drive shaft 20. Obviously, other means to prevent rotation of the non-rotatable tool 34 can be employed; the illustrated shape is easy and convenient to make.

Between the rim 51 and the main body of the non-rotatable tool 34 is a compliance part 52 which is elastically stretchable in the direction of the rotational axis of the tool drive shaft 20, and tends to restrain the tool in the retracted position shown in FIG. 5. Within this part 52 the tool 34 has return-limit rim 53 which comes to rest on the lower confronting surface 54 of the lower housing part 30 when the non-rotatable tool is in the fully retracted position shown in FIG. 5. At the lower end this tool tapers to a tip 55, for interproximal dental use, and a duct 57 which registers with the bore 40 in the tool drive shaft 20 conducts an oral or dental treatment agent (when present) to ducts 58,58 exiting near the tip 55. The bore 50 which receives the tool engagement disc 26 and shaft 20 has a diameter similar to that of the cylindrical peripheral surface 27 of the tool engagement disc, so that the latter disc can rotate within the bore 50 while making only slight contact with the walls of the bore. The bottom wall 56 of the bore 50 is slanted relative to the rotational axis of the tool drive shaft 20, at an angle which may be the same as the angle between the tool engagement disc 26 and that axis; however, these two angles need not necessarily be the same. Owing to the elasticity of the compliance part 52, the bottom wall 56 is at all times in contact with the limited portion 60 of the tool engagement disc which extends the greatest distance from the housing 42, 30. As the tool drive shaft rotates, that portion 60, which may be considered the contact point for driving the non-rotatable tool, moves in a circular path on the bottom wall 56, around the axis of rotation of the tool drive shaft. When the contact point 60 is at the part of the bottom wall 56 which is furthest removed from the rim 51, the tool is in its fully-retracted position, as is shown in FIG. 5. When the contact point 60 is at the part of the bottom wall which is nearest to the rim 51, the tool is in its fully-extended position, as is shown in FIG. 6. As the tool drive shaft 20 is rotated, the non-rotatable tool cyclically extends and retracts, thereby executing an oscillatory motion parallel to the axis of the tool drive shaft. This motion is suitable for dental treatment use as an interproximal stimulator.

It will be observed in FIG. 6 that when the tool 34 is in its fully-extended position the tool engagement disc 26, the bottom wall 56 and the wall of the aperture 50 define a chamber 62 which has its maximum volume. It will likewise be observed in FIG. 5 that when the tool 34 is in its fully-retracted position this chamber 62 has its minimum volume. During oscillation of the non-rotating tool 34, the volume of chamber 62 changes cyclically between the maximum and minimum limits, and the chamber is therefore useful as a pump. Recalling that the access opening 46 to the passage 44 may be fitted with a valve which allows fluid passage only into the bore 40 in the tool-drive shaft 20, the pump can be employed during expanding volume of the chamber 62 to bring a dental or oral treatment agent into the chamber via that bore. For that purpose, the exit ends of ducts 58 may be formed as slit-valves 59 (shown closed in FIG. 6), to reduce the opportunity of air to enter the chamber 62 during expansion of its volume. During contracting of the volume of the chamber 62, the access passage 46 will be closed and the treatment agent will be expelled through the ducts 58,58. To facilitate the pump action described, the lower end of the shaft 20 near the extremity 28 should fit loosely in the recess 56' that is shown in the bottom wall 56.

A one-way valve 64 is shown in the access opening 46 in FIG. 5, as an example of a suitable valve that is inexpensive to make. A tube 66, through which a supply of dentifrice or other dental or oral treatment agent may be furnished, has an end 68 which is closed but for a slit 64, fitted into the access opening 46, which functions as a socket for the end 68. When pressure in the tube 66 exceeds pressure in the connecting passage 44, the treatment agent will force the slit 64 open and the treatment agent will flow into the bore 40. This pressure condition can be brought about by applying increased pressure in the tube 66, as by an external pump (not shown), or by reducing pressure in the bore 40, as by expanding the volume of the chamber 62, in the manner described above; or both forces may be employed simultaneously.

Figure 7:
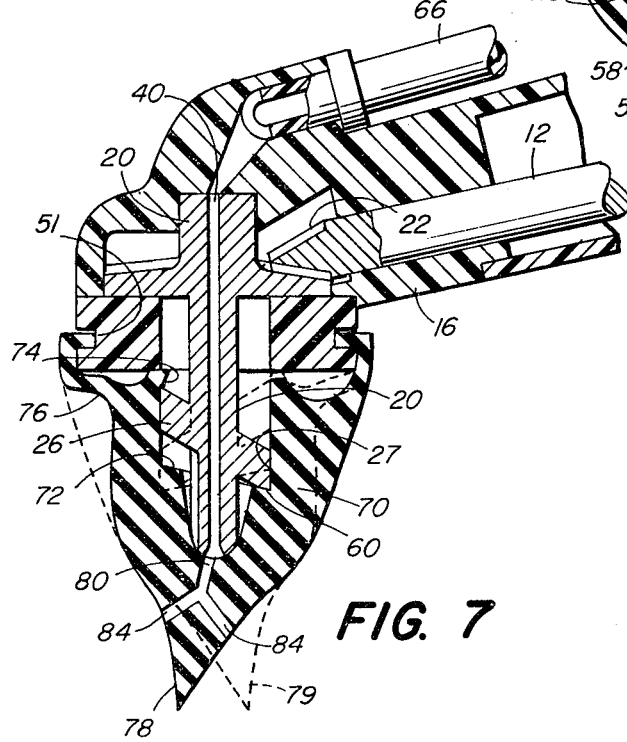
FIG. 7 is a section like FIG. 4, 5 or 6 showing a non-rotating tool that is adapted to execute a nutational motion.

FIG. 7 shows another embodiment of a non-rotatable tool 70, which resembles the non-rotatable tool 34 except that the bottom wall 72 of its bore 74 is not slanted relative to the rotational axis of the tool-drive shaft 20. That is, the contact point 60 of the tool engagement disc 20 runs in a circular path on the bottom wall which, in the absence of stretching by the disc 26, is everywhere the same distance from the rim 51. When the tool 70 is installed on the groove 31 in the boss 32, the tool engagement disc stretches the compliance part 76 in a limited region corresponding to the location of the contact point 60 on the bottom wall 72, displacing the tip 78 away from the rotational axis of the tool drive shaft 20. The bottom wall 72 has a recess 82 in it to receive loosely the extremity 28 of the tool drive shaft 20, and the mating duct 80 in the tool 70 is opened sufficiently to receive a treatment agent from the bore 40, so that as the shaft 20 rotates the tip 78 will execute a nutational motion while receiving the treatment agent and dispensing it through ducts 84. The dotted line 79 illustrates a position in the nutational cycle of the tip 78. The cylindrical surface 27 of the tool engagement disc 26 can be maintained in contact with the wall of the bore 74 sufficiently to confine the treatment agent to the chamber 86 between the disc 26 and the bottom wall 72. In this case, it will be observed that the volume of that chamber 86 remains more nearly constant than does the volume of the chamber 62 in FIGS. 5 and 6.

Figure 8:
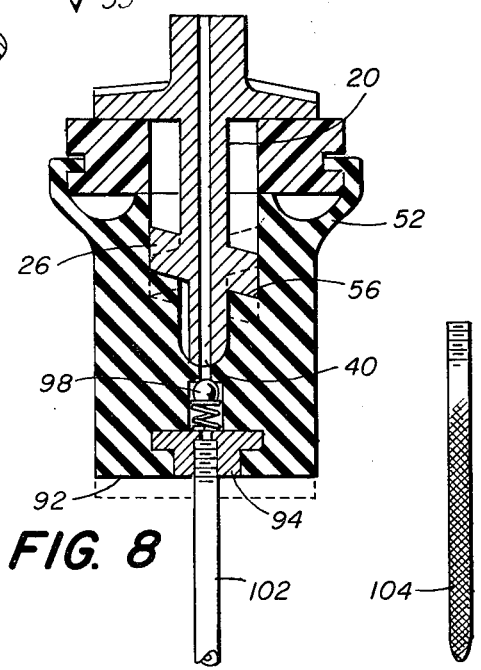
FIG. 8 illustrates a variation of the non-rotational tool of FIGS. 5 and 6 as adapted for endodontal use.
Figure 8A:
FIG. 8A shows a tool that can be substituted in FIG. 8.

FIG. 8 and 8A show an embodiment of the invention employing a variation of the second tool 34 in FIGS. 5 and 6 that is suitable for use in endodontal work. The remote portion of the tool, beyond the compliance part 52, including the pump chamber 62, is fitted at the end 92 with a socket 94 through which a duct 96 communicates with the pump chamber. A one-way valve 98 is fitted in the duct, for passing fluid out of the pump chamber 62 when the volume of the chamber is contracting; this valve closes when the volume of the chamber is expanding. A tube 102 is removably fitted in the socket for carrying fluid expressed from the pump chamber to a root canal in a tooth under treatment (not shown). A material intended to be introduced into the root canal is supplied, for example, through the bore 40 from a source (not shown) via the one-way valve 64 at access opening 46, as shown in FIG. 5.

A reamer 104, useful for preparing a tooth for root canal treatment, can be substituted for the tube 102. In that event, the duct 96 will be plugged and the pump action of chamber 62 will not be used, but the reamer will execute the oscillatory motion parallel to the rotational axis of the drive shaft 20 that is described above with reference to FIGS. 5 and 6. For endodontal purposes, the amplitude of this motion may desirably be in the range 2 to 3 millimeters. This can be achieved by choosing appropriate angles between the tool engagement disc 26 and the shaft 20, and between the bottom wall 56 and the shaft axis. As is mentioned above, the shaft 20 can be made separable from the geared disc 28 (FIG. 2A), enabling the user to select an appropriate angle for the tool engagement disc, depending on the use to which the apparatus is to be put.

Figure 9:
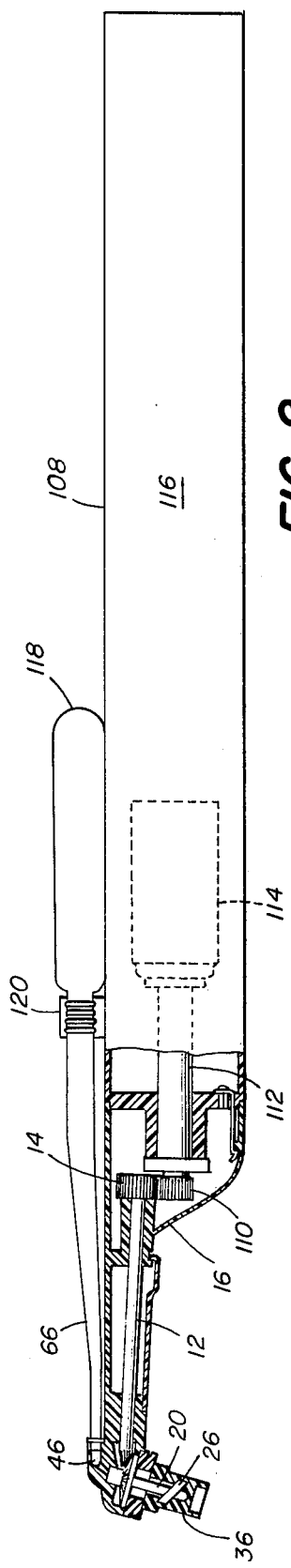
FIG. 9 is an outline of one form of hand-held motor drive to which the invention can be attached.

FIG. 9 is a general illustration of a tool drive apparatus of the invention, as illustrated in FIG. 1 with the rotating tool 36 in place, attached to a housing 108 enclosing batteries 116 and an electric motor 114 having a shaft 112 fitted at its remote end with a driving gear 110 to which the gear 14 of transmission shaft 12 is meshed. Mounting means for detachably holding dental and other tools to a housing encasing a motor with or without batteries (the latter being, if desired, fitted with means to charge or recharge the batteries) are by now well-known, and are not illustrated. A flexible bottle 118 for supplying, for example, a dentifrice to the rotatable tool 36 via a tube 120 to the access opening 46 is also known per se in the prior art. A clamp 120 is suggested to hold such a device in place.

The illustration in FIG. 9 is by way of example only, and is in no sense intended to suggest any limitation on the uses to which the invention may be put. For example, tools having abrasive or felt-like surfaces, and treatment agents having abrasive or polishing properties, can be used in the laboratory, to aid in preparing crowns, bridges and dentures, or in the manufacture of jewelry. It is contemplated that all parts of the invention as illustrated in the drawings, except the transmission shaft 12 and the geared disc 28 and the tool-drive shaft 20 with tool engagement disc 26 may be made of plastics or rubber materials when the invention is intended for domestic use, as a dental care device, as to brush the teeth and to provide superior inderdental stimulation. On the other hand, it is contemplated that a more rugged professional version of the invention, or one requiring greater attention to miniaturization, will be made entirely, or more nearly entirely, of various metals, some of which may be selected for high tensile strength and/or corrosion resistance. Application of the invention to endodontal practice, for example, would require attention to miniaturization, as well as to ruggedization and sterilization. It is therefore to be understood that the description of embodiments herein is by way of example only, and not intended to limit the claims that follow.

I claim:

1. A tool operating apparatus for driving alternatively at least a first tool and a second tool from a single tool driving means to which each of said tools can be removably coupled, in which the tool driving means comprises a rotatable shaft and a support in which the shaft is journaled for rotation around its longitudinal axis, and tool engagement means fixed to the shaft, the first tool having a first aperture for receiving the shaft and means in the first aperture to engage the tool engagement means for rotating the first tool with the shaft, the second tool having a second aperture for receiving the shaft and the tool engagement means, and means on the second tool to engage the support so as to hold the second tool non-rotatably fixed to said support, the shaft and the tool engagement means being free to rotate relative to the second tool within the second aperture, and means in the second aperture for coupling with the tool engagement means to drive the second tool in an oscillatory path relative to said axis during rotation of the shaft in the second aperture.

2. A tool operating apparatus according to claim 1 in which the rotatable shaft has an axially-oriented passage through which a fluid can be passed, each of said tools having duct means for receiving fluid from said passage and dispensing such fluid to a work object, unidirectional valve means associated with said passage for supplying fluid to a tool, at least said second tool including pump means cooperative with said tool engagement means for receiving such fluid and dispensing the same through said duct means.

3. A tool operating apparatus according to claim 2 comprising further unidirectional valve means associated with the duct means of at least said second tool for passing fluid from said pump means through said duct means for dispensing the same.

4. For use in the apparatus according to claim 1, a second tool having a hollow body portion around said second aperture, attachment means at the mouth of the second aperture to engage said support, said hollow body portion including a region that is elastically stretchable in the direction of said axis, the portion of said second tool remote from the attachment means being adapted to move in said oscillatory path.

5. A tool according to claim 4 in which said remote portion is tapered toward a point.

6. A tool according to claim 4 including socket means in said remote portion for detachably receiving a further tool component.

7. A tool operating apparatus according to claim 1 in which the tool engagement means is a disc centrally affixed to the drive shaft, said disc making an acute angle with the longitudinal axis of the drive shaft.

8. A first tool for use in the apparatus of claim 7, having a socket in the first aperture for receiving the outer peripheral portion of said disc and thereby engaging the drive shaft for rotating the first tool with the drive shaft.

9. A second tool for use in the apparatus according to claim 7 having a hollow body portion in which the second aperture is cylindrical and has a diameter such that said disc can rotate within the walls of the second aperture, said hollow body portion including a region that is elastically stretchable in the direction of the longitudinal axis of the drive shaft, the support engagement means of the second tool thereby holding said bottom wall resiliently in contact with a limited contact region on said disc which moves in a circular locus on said bottom wall during rotation of the drive shaft, whereby the portion of said second tool remote from the support engagement means can be driven in an oscillatory path relative to said axis.

10. A second tool according to claim 9 in which the bottom wall of the second aperture is substantially in a plane that makes an acute angle with the longitudinal axis of the drive shaft, whereby said oscillatory path is substantially parallel to said axis.

11. A tool according to claim 10 in which said remote region is tapered toward a point.

12. A tool according to claim 10 including socket means in said remote portion for detachably receiving a further tool component.

13. A tool operating apparatus according to claim 2 in which the tool engagement means is a disc centrally affixed to the drive shaft, said disc making an acute angle with the longitudinal axis of the drive shaft, in combination with a second tool in which the bottom wall of the second aperture is substantially in a plane that makes an acute angle with said axis, said second tool having a hollow body portion including, between said means to engage the support and the portion of said tool including said bottom wall that is remote from said support, a region that is elastically stretchable in the direction of said axis, the support engagement means thereby holding said bottom wall resiliently in contact with a limited contact region on said disc which moves in a circular locus on said bottom wall during rotation of the drive shaft, whereby said remote portion can be driven in an oscillatory path that is substantially parallel to said axis, said disc and said bottom wall forming in the included portion of said second aperture a substantially enclosed chamber the volume of which changes cyclically as said drive shaft rotates said disc within said second chamber to constitute said pump means, said passage communicating with said chamber from said shaft, and said chamber communicating with said duct means.

14. A second tool according to claim 9 in which the bottom wall of the second aperture has a circular locus for contact with said disc, which locus lies substantially in a plane making a right angle with the longitudinal axis of the drive shaft, whereby said remote portion can execute a nutational motion around said axis.

15. In a dental treatment device for driving alternatively at least a first tool and a second tool, each tool being intended to execute a different form of motion, tool driving means to which each of said tools can be removably coupled, the driving means including a drive shaft, a support for said shaft in which the shaft is journaled for rotation around its longitudinal axis, and tool-engagement means fixed to a portion of the shaft extending from the support, the first tool having a first aperture to receive said extending portion of the shaft and means in the first aperture to engage said tool engagement means for rotating the first tool with the shaft, the second tool having a second aperture to receive said extending portion of the shaft and means resiliently to engage said support so as to hold the second tool non-rotatably fixed to the support, whereby the shaft can rotate within said second aperture relative to the second tool, and means in the second aperture for coacting with the shaft during rotation thereof within the second aperture to drive the second tool in an oscillatory path relative to said axis.

16. A dental treatment device according to claim 15 in which the support has a tool-engaging boss for engaging the second tool, the second tool being made of material selected from rubber, plastics material or the like having a hollow body portion around said second aperture, a portion at the mouth of said aperture including a flexible surround at said mouth with means to interlock with the boss in a manner to hold the second tool fixed to the support while preventing rotation of the second tool around the axis of the shaft, a part of the second tool remote from said mouth tapering externally toward a point for inter-proximal dental stimulator use.

17. A dental treatment device according to claim 15 in which the drive shaft has an axial passage through which a fluid can be passed, unidirectional valve means in the flow path of said fluid, means fixable to the support for introducing a fluid into said passage through said valve means, each of the first and second tools having duct means for receiving such fluid from said passage at the end of the shaft remote from the support, for dispensing such fluid when present through the tool being used.

18. A dental treatment device according to claim 15 in which said tool engagement means is a disc affixed to the drive shaft between the support and the end of the shaft which is remote from the support, said disc making an acute angle with the longitudinal axis of the drive shaft.

19. In combination in the dental treatment device according to claim 18, a first tool having a socket in said first aperture for receiving the outer peripheral portion of said disc and thereby engaging the drive shaft for rotating the first tool with the shaft.

20. In combination in the dental treatment device according to claim 18, the second aperture in the second tool being cylindrical and having a diameter such that said disc can rotate within the side-walls thereof, the bottom wall of said second aperture being substantially in a plane making an acute angle with the longitudinal axis of the drive shaft, the engagement means of the second tool holding said bottom wall resiliently in contact with a limited region on said disc which moves in a circular locus on the bottom wall during rotation of said drive shaft, whereby said second tool is driven in an oscillatory path that is substantially parallel to said axis.

21. A dental treatment device according to claim 20 in which the drive shaft has an axial passage through which a fluid can be passed, unidirectional valve means in the flow path of said fluid, means fixable to the support for introducing a dental treatment agent in fluid form into said passage through said valve means, the diameter of said second aperture being sized such that the side walls thereof make contact with the periphery of said disc during rotation of said drive shaft within said second tool, the portion of said second aperture between the disc and the bottom wall thereby forming a substantially enclosed chamber the volume of which changes cyclically as the drive shaft rotates within the second tool, said axial passage communicating with said chamber, and the second tool having duct means from said chamber to the exterior of the second tool for dispensing such agent when present, said second chamber cooperating with said unidirectional valve means during rotation of the drive shaft to eject such agent when present through said duct means.

22. In combination in the dental treatment device according to claim 18 said second aperture in the second tool being cylindrical and having a diameter sized such that said disc can rotate within the side walls thereof, the bottom wall of said second aperture having a circular locus for contact with said disc which locus lies in a plane making substantially a right angle with the longitudinal axis of said drive shaft, the engagement means of said second tool holding said bottom wall resiliently against a limited contact region on the disc which moves in said circular locus during rotation of the drive shaft so as to apply force to stretch said engagement means cyclically around said axis, thereby to force said second tool to execute a nutational motion around said axis.

23. A tool operating apparatus comprising a rotatable shaft and a support in which the shaft is journaled for rotation around its longitudinal axis, a disc centrally affixed to the shaft at an acute angle to said axis, a tool member having a cylindrical aperture opening at one end for receiving said shaft and disc, means at the open end of the tool member for non-rotationally affixing the tool member to the support so that the shaft and disc can rotate in the aperture relative to the tool member, the aperture having a bottom wall that is substantially in a plane at an acute angle to said axis, a portion of the tool member between the support and said bottom wall being elastically stretchable in the direction of said axis and acting to hold the bottom wall in contact with a limited region of the disc which describes a circular path on the bottom wall when the shaft is rotated, so as to cause the portion of the tool member remote from the support to execute oscillatory motion substantially parallel to said axis.

24. A tool operating apparatus according to claim 23 including socket means in said remote portion for detachably receiving a further tool member such as a reamer, file or the like which makes use of said oscillatory motion.

25. A tool operating apparatus according to claim 23 in which the rotatable shaft has an axially-oriented passage through which a fluid can be passed and the tool member has duct means in said remote portion for receiving such fluid, when present, from said passage, the disc and said bottom wall forming in the included portion of said cylindrical aperture a substantially enclosed chamber the volume of which changes cyclically as the drive shaft rotates the disc in said aperture, the passage in the shaft communicating with said chamber, unidirectional valve means associated with said passage for admitting fluid to said chamber upon expansion of said volume; the chamber communicating with said duct means, and unidirectional valve means in the duct means for passing fluid from said chamber upon contraction of said volume.

26. A tool operating apparatus according to claim 25 including a tubular extension from said duct means providing a fluid conduit to a remote location.

27. A tool operating apparatus according to claim 26 including socket means in said remote portion, said duct means opening through the socket means, and said tubular extension being removably fitted in the socket means.

28. A tool operating apparatus according to claim 25 including socket means in said remote portion, said duct means opening through said socket means, said socket means being adapted to receive alternatively a tubular extension of said duct means for providing a fluid conduit that oscillates and supplies fluid, when present, under pressure from said chamber during contraction of its volume, or a solid further tool member such as a reamer, file or the like which makes use of said oscillatory motion.

29. A tool operating apparatus according to claim 28 for endodontal use including means to supply a fluid treatment agent into said passage, said chamber being adapted to pump said fluid when present into a root canal through said tubular extension, and said solid further tool being adapted for forming a root canal, the angles of said disc and bottom wall relative to said axis being selected to provide an amplitude of said oscillation that is suitable for endodontal use.

30. A tool operating apparatus for driving alternatively and selectively one of a variety of different tools from a single rotatable shaft that is journaled in a support for rotation around its longitudinal axis, comprising a tool driving and mounting means affixed to the shaft for driving tools of a first type that are intended to rotate with the shaft when mounted thereon, and a second tool mounting means affixed to the support for mounting tools of a second type that are not intended to rotate with the shaft but are intended to coact with said tool driving means on the shaft for drive purposes, said second tool mounting means providing a non-rotative attachment for holding a tool of said second type non-rotatively attached to said apparatus in engagement with said tool driving means of said shaft for driving a tool of said second type in an oscillatory mode.

31. A tool operating apparatus for driving alternatively a variety of tools from a single operator, means to couple a first tool to said operator for motion exclusively in a first mode, and means to couple a second tool to said operator for motion exclusively in a second mode.

32. An apparatus according to claim 31 in which one of said tools is adapted when coupled to said operator to execute motion in an oscillatory mode.

33. An apparatus according to claim 32 including conduit means in said operator to supply a dental treatment agent in fluid form to said tools, and means to pump said agent via said tool executing motion in an oscillatory mode to a recipient of treatment.

34. An apparatus according to claim 33 in which said tool executing motion in an oscillatory mode includes a suction unit operable during said motion in an oscillatory mode to pump said agent.

* * * * *